US012599300B2

(12) United States Patent
Tata et al.

(10) Patent No.: US 12,599,300 B2
(45) Date of Patent: Apr. 14, 2026

(54) LARYNGOSCOPE WITH PHYSIOLOGICAL PARAMETER INDICATOR

(71) Applicant: Covidien AG, Neuhausen am Rheinfall (CH)

(72) Inventors: Derek Scot Tata, Loveland, CO (US); Peter Douglas Colin Inglis, Boulder, CO (US); Craig Allen Patton, Boulder, CO (US); Michael Ng, Kowloon (HK); George R. Winski, Fort Collins, CO (US); Caitlyn Anne Hughes, Westminster, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 299 days.

(21) Appl. No.: 17/076,567

(22) Filed: Oct. 21, 2020

(65) Prior Publication Data

US 2021/0128033 A1 May 6, 2021

Related U.S. Application Data

(60) Provisional application No. 62/928,173, filed on Oct. 30, 2019.

(51) Int. Cl.
*A61B 1/267* (2006.01)
*A61B 1/00* (2006.01)
(Continued)

(52) U.S. Cl.
CPC ............ *A61B 1/267* (2013.01); *A61B 1/0004* (2022.02); *A61B 5/0013* (2013.01);
(Continued)

(58) Field of Classification Search
CPC ... A61B 5/0013; A61B 5/0015; A61B 5/0077; A61B 5/024; A61B 5/14551; A61B 5/742; A61B 5/7455; A61B 5/7475
See application file for complete search history.

(56) References Cited

U.S. PATENT DOCUMENTS 8,798,700 B1 * 8/2014 Heaton, II ............. A61B 5/684
600/323
10,264,958 B2 4/2019 McWilliam et al.
(Continued)

FOREIGN PATENT DOCUMENTS

WO 2011060445 A1 5/2011

OTHER PUBLICATIONS

Lee, Hyung-Chul et al.; "Real-time endoscopic image orientation correction system using an accelerometer and gyrosensor," Plos One, 12(11), Nov. 3, 2017, 12 pgs.
(Continued)

*Primary Examiner* — Jennifer Pitrak McDonald
*Assistant Examiner* — Moussa Haddad

(57) ABSTRACT
A laryngoscope system includes a monitor having communication circuitry and that communicates physiological parameter information to communication circuitry of a paired laryngoscope. The paired laryngoscope includes a camera and a display configured to display image data from the camera. A processor of the laryngoscope is programmed to generate instructions to provide a physiological parameter indicator via the laryngoscope based on the received physiological parameter information from the monitor.

22 Claims, 8 Drawing Sheets

(51) Int. Cl.
    *A61B 5/00*           (2006.01)
    *A61B 5/024*        (2006.01)
    *A61B 5/1455*      (2006.01)

(52) U.S. Cl.
    CPC .......... *A61B 5/0015* (2013.01); *A61B 5/0077*
       (2013.01); *A61B 5/024* (2013.01); *A61B*
       *5/14551* (2013.01); *A61B 5/742* (2013.01);
       *A61B 5/7455* (2013.01); *A61B 5/7475*
       (2013.01)

(56) References Cited

U.S. PATENT DOCUMENTS

| | | | |
|---|---|---|---|
| 2005/0038348 A1 | 2/2005 | Avicola et al. | |
| 2006/0220614 A1* | 10/2006 | Abe ................... | A61B 1/00045 |
| | | | 320/114 |
| 2008/0300464 A1 | 12/2008 | Dhingra et al. | |

| | | | |
|---|---|---|---|
| 2011/0178508 A1* | 7/2011 | Ullrich ............. | A61B 17/00234 |
| | | | 606/1 |
| 2015/0080655 A1 | 3/2015 | Peterson et al. | |
| 2017/0020627 A1* | 1/2017 | Tesar ................... | A61B 90/361 |
| 2017/0135555 A1* | 5/2017 | Yoshizaki .......... | A61B 1/00055 |
| 2018/0192865 A1* | 7/2018 | McGrath ................. | A61B 1/05 |
| 2019/0133430 A1 | 5/2019 | Inglis et al. | |
| 2019/0142262 A1* | 5/2019 | Inglis ................. | A61B 1/00052 |
| | | | 600/188 |
| 2019/0224434 A1* | 7/2019 | Silver ................. | A61N 1/3925 |
| 2019/0298952 A1 | 10/2019 | Taniguchi et al. | |
| 2019/0318820 A1 | 10/2019 | Rosenblatt et al. | |
| 2021/0233648 A1* | 7/2021 | Kamon ................. | G16H 30/20 |

OTHER PUBLICATIONS

International Search Report and Written Opinion for PCT Application No. PCT/EP2020/080491, mailed Jan. 19, 2021, 13 pages.

* cited by examiner

200

ESTABLISH  COMMUNICATION  LINK  BETWEEN
MONITOR  AND  LARYNGOSCOPE                    ——202

RECEIVE  PHYSIOLOGICAL  PARAMETER  INFORMATION
AT  LARYNGOSCOPE  FROM  MONITOR                ——204

GENERATE  PHYSIOLOGICAL  PARAMETER  INDICATOR
INSTRUCTIONS  BASED  ON  PHYSIOLOGICAL  PARAMETER    ——206
INFORMATION  VIA  LARYNGOSCOPE

LARYNGOSCOPE WITH PHYSIOLOGICAL PARAMETER INDICATOR

CROSS-REFERENCE TO RELATED APPLICATIONS

The present application claims priority to and the benefit of U.S. Provisional Application No. 62/928,173, filed on Oct. 30, 2019, the disclosure of which is incorporated by reference in their entirety for all purposes.

BACKGROUND

The present disclosure relates generally to medical devices and, more particularly, to laryngoscope methods and systems that permit an indication of physiological parameter information communicated from one or more medical monitoring devices.

This section is intended to introduce the reader to various aspects of art that may be related to the present disclosure, as described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, tracheal tubes may be used to control the flow of air or other gases through a patient's trachea and into the lungs, for example during mechanical ventilation. Such tracheal tubes may include endotracheal (ET) tubes, tracheostomy tubes, or transtracheal tubes. Laryngoscopes are in common use for the insertion of endotracheal tubes into the tracheas of patients during medical procedures. Laryngoscopes may include a light source to permit visualization of the patient's airway to facilitate intubation, and video laryngoscopes may also include an imager, such as a camera. The laryngoscope, when in use, extends only partially into the patient's airway, and the laryngoscope may function to push the patient's tongue aside to permit a clear view into the airway for insertion of the endotracheal tube.

SUMMARY

Certain embodiments commensurate in scope with the originally claimed subject matter are summarized below. These embodiments are not intended to limit the scope of the disclosure. Indeed, the present disclosure may encompass a variety of forms that may be similar to or different from the embodiments set forth below.

In one embodiment, a laryngoscope includes a camera and a display configured to display image data from the camera. The laryngoscope also includes communication circuitry configured to receive physiological parameter information from a paired monitor. The laryngoscope also includes a processor programmed to generate instructions to provide a physiological parameter indicator via the laryngoscope based on the received physiological parameter information from the paired monitor.

In an embodiment, a system, e.g., a laryngoscope system, includes a monitor comprising monitor communication circuitry and configured to communicate physiological parameter information. The system also includes a laryngoscope having a camera and a display configured to display image data from the camera. The laryngoscope also includes communication circuitry configured to receive physiological parameter information from the monitor. The laryngoscope also includes a processor programmed to generate instructions to provide a physiological parameter indicator via the laryngoscope based on the received physiological parameter information from the paired monitor.

In an embodiment, a method is provided that includes the steps of pairing a laryngoscope and a monitor to communicate wirelessly; transmitting physiological parameter information from the monitor to the laryngoscope; and causing a physiological parameter indicator to be displayed on the laryngoscope or an indicator element of the laryngoscope to be activated based on the physiological parameter information.

Features in one aspect or embodiment may be applied as features in any other aspect or embodiment, in any appropriate combination. For example, any one of system, laryngoscope, controller, introducer, or method features may be applied as any one or more other of system, laryngoscope, monitor, or method features.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
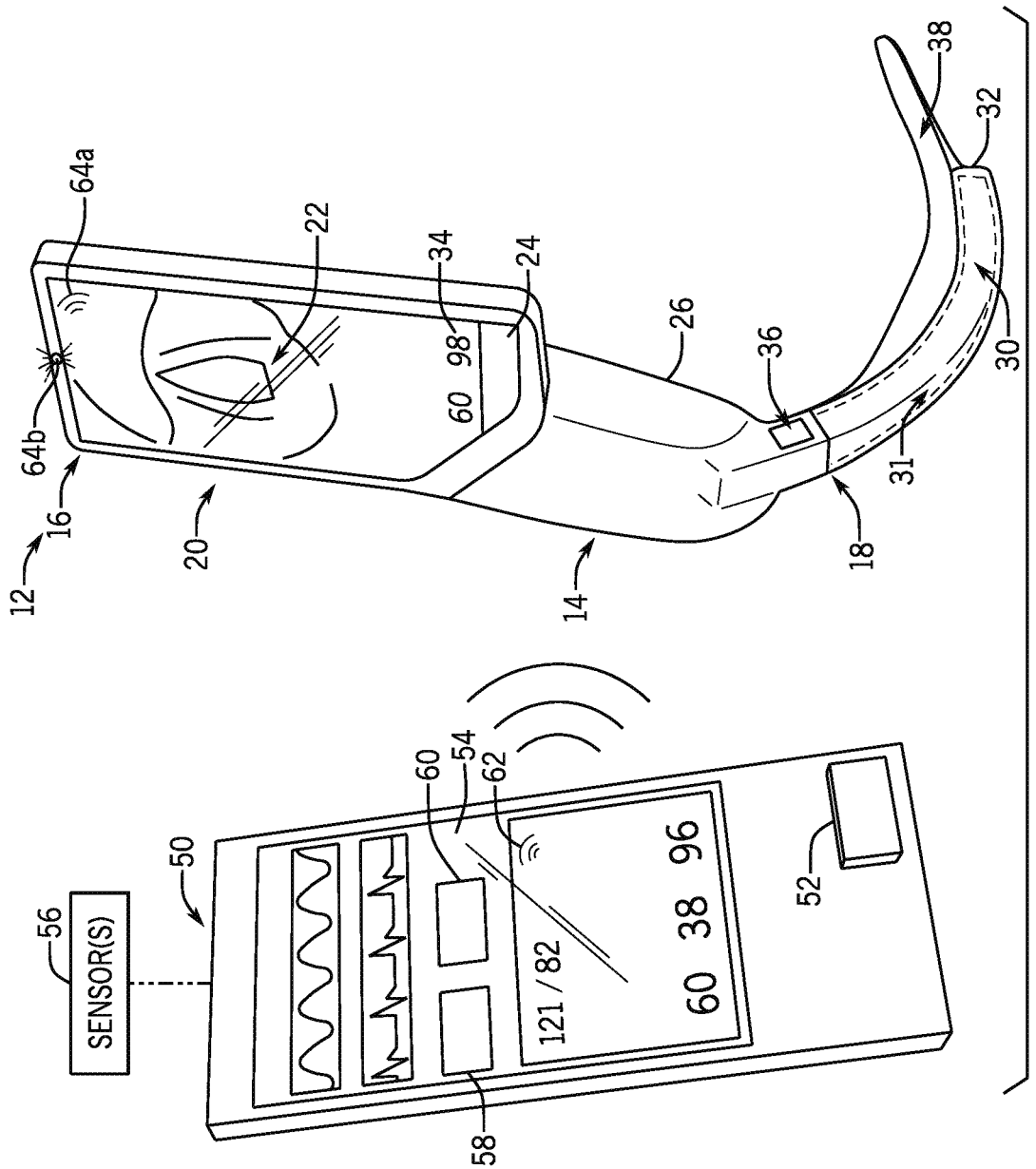
FIG. 1 is a perspective view of a laryngoscope system including a laryngoscope communicatively coupled to a medical monitor, in accordance with an embodiment of the present disclosure.

In operation, a clinician may use a laryngoscope to assist in intubation, e.g., to visualize a patient's airway to guide advancement of the distal tip of an endotracheal tube through the patient's oral cavity, through the vocal cords, into the tracheal passage. Visualization of the patient's anatomy during intubation may help the medical clinician to avoid damaging or irritating the patient's oral and tracheal tissue, and avoid passing the endotracheal tube into the esophagus instead of the trachea. The clinician performing the intubation, e.g., an anesthesiologist, may obtain a direct view of the patient's anatomy by using a laryngoscope to open the patient's mouth and lift the tongue. If the clinician is using a video laryngoscope that includes a camera, the clinician may also or alternatively obtain an indirect view of the patient's anatomy by viewing the images captured from the camera and displayed on a display screen. The display screen may be integrated with the laryngoscope, such as mounted on the handle of the laryngoscope, within the clinician's natural viewing angle looking toward the patient, to enable the clinician to view the display while manipulating the laryngoscope and endotracheal tube in real time. Accordingly, the user may view the integrated display to guide the endotracheal tube in the airway while also maintaining visual contact with the airway entry to assist in successful intubation.

The laryngoscope may be operated with a single hand (such as the operator's left hand) while the other hand (such as the user's right hand) grips the endotracheal tube and guides it forward into the patient's airway. The user may view advancement of the endotracheal tube on the display screen in order to guide the endotracheal tube into its proper position. The user adjusts the viewing angle by manipulating and orienting the laryngoscope within the patient's oral cavity, to account for patient-to-patient variability of anatomy in the airway. By providing the visualization information within a single line of sight, the user may remain focused and oriented on the airway navigation and the intubation procedure without being distracted by other medical procedures that may be simultaneously occurring, such as emergency or surgical procedures.

During an intubation procedure, a clinician performing the intubation may balance a desired rapid intubation and corresponding initiation of mechanical ventilation with navigation challenges, such as avoiding esophageal insertion or guiding the endotracheal tube through a difficult airway. In cases in which the intubation is not successfully completed within a certain period of time (e.g., based on the clinician's experience and comfort level), the attempt is interrupted and the patient may be temporarily ventilated using an alternate source of oxygen (e.g., manual ventilation, bag vent) until such time as the clinician may try again. The conditions under which an intubation attempt is halted to allow temporary ventilation and reoxygenation may vary from patient-to-patient. However, a dip in the patient's measured oxygen saturation value during the intubation procedure and/or an elapsed time of the intubation procedure may be indicative that the intubation procedure should be halted until oxygenation returns to desired levels. While various multi-parameter monitoring devices that provide oxygen saturation information may be available within the patient environment, the clinician may not wish to divert attention from the view of the video laryngoscope during a time-sensitive intubation procedure. Further, the displays of such monitoring devices are designed with multiple types of clinicians and clinical situations in mind, and the relevant information pertinent to the intubation procedure may not be quickly ascertained based on a quick glance.

Provided herein are laryngoscope techniques that provide feedback related to one or more physiological parameters of interest for the laryngoscope user and that may be relevant to airway navigation. The laryngoscope functions to provide physiological parameter information to the clinician in a manner that quickly conveys the information of interest and without distracting the clinician from an ongoing airway navigation procedure. Accordingly, while the physiological parameter information may be communicated by a medical monitor to the laryngoscope according to the present techniques, the manner of indicating the physiological parameter may differ between these devices, with the medical monitor providing more complex displays and parameter display options and with the laryngoscope providing relatively simpler indicators that, in embodiments, may not be able to be customized via user input. The laryngoscope operates to display the information on a display or to provide one or more haptic, visual, and/or audio indicators related to the physiological parameter. The physiological parameter feedback may, in embodiments, be provided in conjunction with an uninterrupted view of the airway through the laryngoscope camera and/or any additional coupled camera, such as an introducer camera, such that the laryngoscope user's line of sight is not diverted from the airway and patient during airway navigation. The laryngoscope may receive the physiological parameter information from a communicatively coupled medical monitoring device as a calculated value or updating series of values reflective of real-time patient conditions such that the values are used to drive display information or visual, audio, or haptic feedback. In an embodiment, the laryngoscope may be programmed with operating instructions that receive the calculated physiological parameter values and use the values as inputs to one or more rules-based notification systems that trigger the physiological parameter indication only when certain limits are violated (e.g., an oxygen saturation below a particular threshold). Accordingly, the disclosed laryngoscope techniques permit communication of physiological parameter information from a medical monitoring device and to a laryngoscope to convey information to a clinician performing an airway navigation procedure.

With the foregoing in mind, FIG. 1 is a perspective view of an embodiment of a laryngoscope system 10. The multifunctional video laryngoscope 12 includes an elongate body 14, which may be ergonomically shaped as a handle to facilitate grip by a user. The body extends from a proximal end 16 to a distal end 18 and includes a display, e.g., a display assembly 20 having a display screen 22. As illustrated, the display assembly 20 is coupled to the proximal end 16 and extends laterally from the body 14 such that a lateral portion 24 of the display assembly 20 extends outwardly away from a housing 26 of the body 14. In the illustrated embodiment, the display assembly 20 may be formed as an integrated piece with the body 14, such that a housing of the display assembly 20 and an exterior of the body 14 are formed from the same material. However, in other embodiments, the display assembly 20 may be formed as a separate piece and adhered or otherwise coupled to the body 14. The display assembly 20 may be fixed relative to the body 14 or may be pivotable, such that an angle or the position of the display assembly 22 may be adjusted by the user.

In an embodiment, the laryngoscope 12 also includes a camera stick 30, which may be coupled to the body 14 at the distal end 18 (either fixedly or removably). In certain embodiments, the camera stick 30 may be formed as an elongate extension or arm (e.g., metal, polymeric) housing an image acquisition device (e.g., a camera) and a light source. The camera stick 30 may also house cables or electrical leads that couple the light source and the camera to electrical components in the body 14, such as the display 20, a computer, and a power source. The electrical cables provide power and drive signals to the camera and light source and relay data signals back to processing components in the body. In certain embodiments, these signals may be provided wirelessly in addition to or instead of being provided through electrical cables.

In use to intubate a patient, a removable and at least partially transparent blade 38 is slid over the camera stick 30 like a sleeve. The laryngoscope blade includes an internal channel or passage 31 sized to accommodate the camera stick 30 and to position a camera of the camera stick 30 at a suitable angle to visualize the airway. In the depicted arrangement, the passage 31 terminates at a closed end face 32 positioned such that a field of view of the camera is oriented through the closed end face 32. The laryngoscope blade 38 is at least partially transparent (such as transparent at the closed end face 32, or transparent along the entire blade 38) to permit the camera of the camera stick 30 to capture images through the laryngoscope blade 38. The camera and light source of the camera stick 30 facilitate the visualization of an endotracheal tube or other instrument inserted into the airway. For example, the captured image from the camera stick 30 is displayed on the display screen 22. In addition, in certain embodiments, one or more physiological parameter indicators 34 may be displayed in conjunction with the captured image. Additionally or alternatively, the physiological parameter indicator may be provided via other feedback elements that are not displayed. For example, one or more physiological parameter indicators may be an audio, visual (e.g., light indicator that is not part of the display screen 22), and/or haptic indicator.

The laryngoscope 12 may be cleaned and reused for multiple patients. The removable blade 38 protects the components such as the camera stick 30 that would otherwise be exposed to the environment of the upper airway, such as coming into contact with tracheal or oral tissue. The distal end 18 of the body 14 of the laryngoscope 12 may include an attachment feature 36 to facilitate removable or reversible coupling of the laryngoscope blade 38 to the body. For example, the attachment feature 36 may include a protrusion on the body 14, which fits demountably into a recess or passageway formed in a corresponding portion of the laryngoscope blade 38, or vice versa. The laryngoscope blade 38, in certain embodiments, may be configured as a disposable single-use device. Accordingly, in certain embodiments, the multifunctional laryngoscope 12 may be provided as a kit that includes one or more laryngoscope blades 38. The laryngoscope blade 38 may be selected to an appropriate patient size and shape based on an estimate or assessment of the patient's airway, size, or condition, or according to procedure type, or clinician preference.

The laryngoscope system 10 may receive transmitted data from one or more devices or systems, such as a monitor 50 (e.g., a medical monitor), a computing system, and/or a hospital data storage system. For example, in an embodiment, in response to detection of a compatible monitor 50 by communication circuitry of the laryngoscope 12, the laryngoscope 12 communicates with the monitor 50 to pair with the monitor and to receive physiological parameter information (e.g., wirelessly streamed physiological parameter information in substantially real-time) from the monitor 50. In certain embodiments, in response to pairing to the monitor 50, the monitor 50 automatically transmits data from a memory of the monitor 50 to the laryngoscope 12 at certain times (e.g., upon powering the laryngoscope 12 and/or the monitor 50 off or on, periodically during the laryngoscopy procedure, upon receipt of a user input, until receipt of an input indicating that the laryngoscopy procedure is complete and/or until certain steps of the laryngoscopy procedure are complete). The physiological parameter information may be displayed on the display screen, as in the illustrated embodiment, and/or indicated by audio, visual, or haptic feedback elements.

The laryngoscope 12 may communicate with the monitor 50 to receive physiological parameter information, e.g., the laryngoscope 12 may be paired with the monitor 50. For example, the laryngoscope 12 and the monitor 50 may include communication circuitry or communication devices (e.g., wireless transceivers) that are configured to establish wireless communication with one another using any suitable protocol. In the illustrated embodiment, an adapter 52 (e.g., wireless adapter, dongle, or bridge device) is provided to facilitate wireless communication between the laryngoscope 12 and the monitor 50 and/or other devices and systems. For example, in the illustrated embodiment, the adapter 52 includes a wireless transceiver that sends information to the laryngoscope 12. The adapter 52 is coupled to the monitor 50 (e.g., by plugging the adapter 52 into a Universal Serial Bus [USB] port of the monitor 50) to relay information or commands between the laryngoscope 12 and the monitor 50. Such a configuration may enable use of the laryngoscope 12 with third-party monitors or multi-parameter monitors. For example, the adapter 52 may be coupled to a first monitor 50 to enable wireless communication (e.g., transfer of physiological parameter information to the laryngoscope 12 from the monitor 50, transfer of an instruction from the monitor 50 to the laryngoscope 12, or the like) between the laryngoscope 12 and the first monitor 50, and the adapter 52 may then be removed from the first monitor 50 and coupled to a second monitor 50 to enable wireless communication between the laryngoscope 12 and the second monitor 50. Thus, the laryngoscope 12 may communicate with (e.g., receive data from) a receiver, which may be the monitor 50 or the adapter 52, for example.

As shown, the monitor 50 includes a display screen 54 (e.g., touchscreen display) that provides information to the clinician and/or that is configured to receive user inputs. For example, the monitor 50 may display physiological parameter information, such as measured parameter values (e.g., heart rate values, oxygen saturation values, blood pressure values, or the like), trend data or variability data derived from the measured parameter values, raw data, waveforms, alarm information, etc., obtained via various physiological sensors 56 that are directly or indirectly coupled to the monitor 50. In one example, the monitor 50 is a multi-parameter monitor that receives inputs from various monitoring devices. In another example, the monitor 50 is a ventilator. In the illustrated embodiment, the monitor 50 may include a user input device 58 (e.g., soft key on the display screen 54 or button) that facilitates pairing with the laryngoscope 12 to communicate physiological parameter information to the laryngoscope 12, and additional user input inputs 60 that permit the caregiver to manipulate the settings or modify the parameters displayed on the display screen 54 or on the laryngoscope 12. For example, the laryngoscope 12 may have a limited user interface, and modification of alarm limits (tolerance within ranges or thresholds) for the physiological parameter indicator may be more easily accomplished via the monitor 50.

In other embodiments, the pairing between the monitor 50 and the laryngoscope 12 is automatically initiated by the laryngoscope 12, e.g., upon powering on. The laryngoscope 12 may transmit a pairing signal that is received by the monitor 50, which confirms the pairing via a handshake. It should be appreciated that the laryngoscope 12 and the monitor 50 may also include ports (e.g., USB ports, Ethernet ports, high-definition multimedia interface [HDMI] ports, optical ports, infrared ports, near field ports, or the like) that permit various components of the system 10 to be coupled to one another and/or to other components (e.g., computing systems or storage systems) via a wired connection.

In some embodiments, the display screen 54 of the monitor 50 may provide a pairing indication 62 that the monitor 50 and the laryngoscope 12 are communicatively coupled to one another. The laryngoscope 12 may provide a corresponding pairing indication 64 (e.g., a displayed indication 64a or a light indication 64b incorporated on or in a housing 26 of the laryngoscope 12). In some embodiments, the laryngoscope 12 may be configured to provide a laryngoscope ID (e.g., numerical or descriptive identifier) to the monitor 50, and the monitor 50 displays the laryngoscope ID on the display screen 54 to permit the medical professional to confirm that the monitor 50 is receiving data from the appropriate laryngoscope 12. In an embodiment, the monitor 50 is configured to pair with only one laryngoscope 12 at a time. In some embodiments, the monitor 50 and/or the laryngoscope 12 may permit the medical professional to provide inputs (e.g., via one or more touchscreen display screens 18, 54) to adjust or to select the appropriate device(s) (e.g., the monitor 50 and the laryngoscope 12) that should communicate with one another during the laryngoscopy procedure. In some embodiments, the laryngoscope system 10 may be configured to provide the physiological parameter information until the pairing between the laryngoscope 12 and the monitor 50 is interrupted, which may be triggered by powering off of the laryngoscope 12 or via a user input on the laryngoscope 12 or the monitor 50 to interrupt the pairing. It should be appreciated that the medical professional may provide various inputs disclosed herein via a voice command to a microphone of the laryngoscope 12. Such configurations may be particularly useful when the laryngoscope system 10 is used in an environment or circumstance in which multiple monitors 50 and/or multiple laryngoscopes 12 are operating simultaneously, for example.

Figure 2:
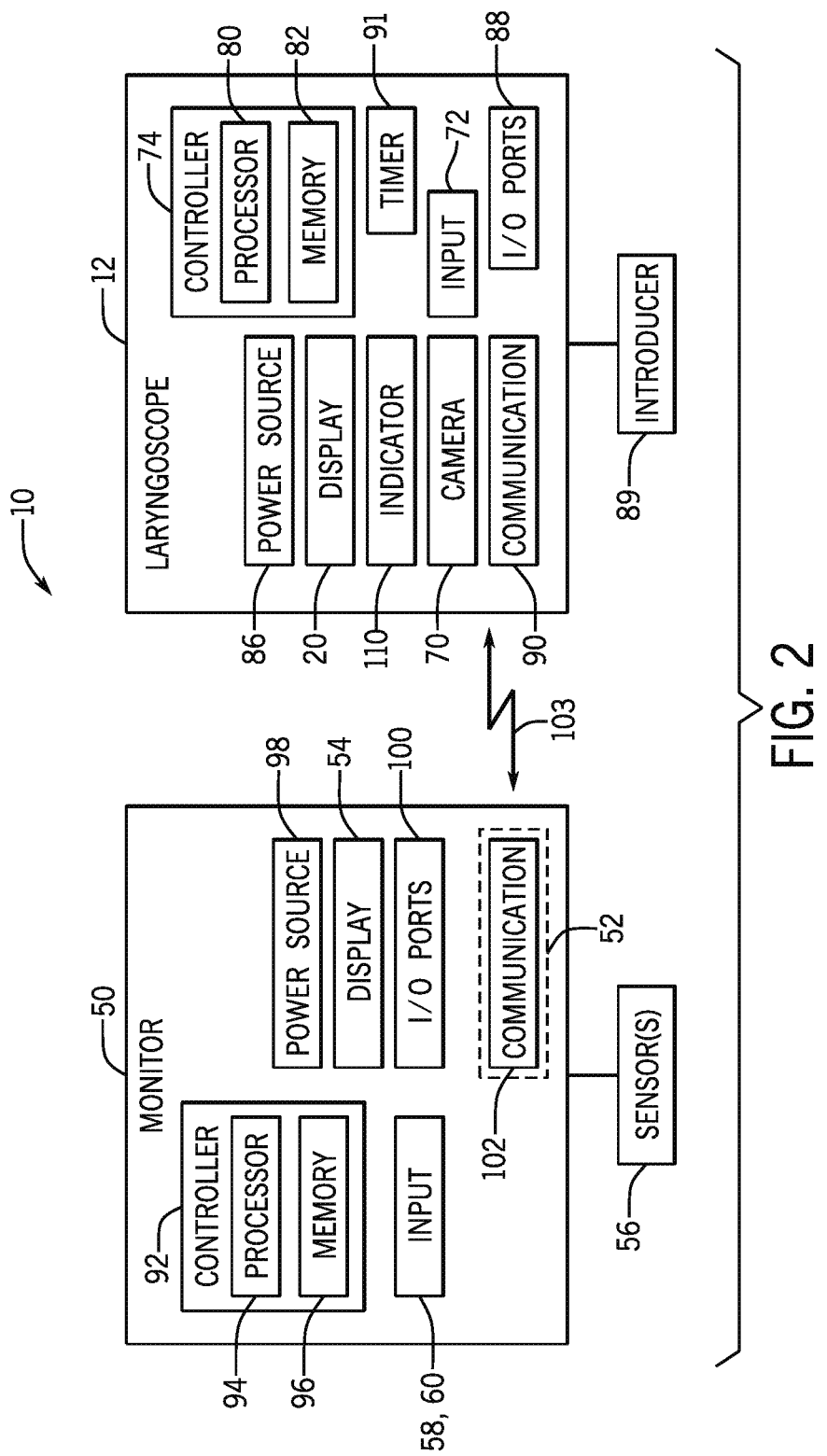
FIG. 2 is a block diagram of the laryngoscope system of FIG. 1, in accordance with an embodiment of the present disclosure.

FIG. 2 is a block diagram of an embodiment of the laryngoscope system 10. As shown, the laryngoscope system 10 includes the laryngoscope 12 and the monitor 50. The laryngoscope 12 and the monitor 50 include various components that facilitate techniques disclosed herein. For example, the laryngoscope 12 may include the display screen 22, a camera 70, and one or more user input devices (e.g., touch sensor) 72, as well as a controller 74 (e.g., electronic controller), one or more processors 80, a hardware memory 82, a power source (e.g., battery) 86, input/output (I/O) ports 88, a communication device 90, and a timer 91. In some embodiments, the timer 91 may track time associated with the physiological parameter information and/or the laryngoscope procedure time, which may be communicated to and/or used by the laryngoscope 12 as part of assessing whether an intubation process should be aborted in conjunction with the physiological parameter information, as provided herein. The timer 91 may be responsive to user inputs (e.g., via the user input 72) that mark an initiation of an intubation procedure. The laryngoscope 12 may be coupled to other devices, such as an introducer 89, via a connector.

The monitor 50 may include the display screen 54, a controller 92 (e.g., electronic controller), one or more processors 94, a hardware memory 96, a power source (e.g., battery or input from external power source) 98, I/O ports 100, and a communication device 102. The power sources 86, 98 may be rechargeable and/or replaceable batteries. The communication devices 90, 102 may be wireless transceivers that are configured to establish wireless communication 103 with one another. By way of example, the communication devices 90, 102 may be configured to communicate using the IEEE 802.15.4 standard, and may communicate, for example, using ZigBee, WirelessHART, or MiWi protocols. Additionally or alternatively, the communication devices 90, 102 may be configured to communicate using the Bluetooth standard or one or more of the IEEE 802.11 standards. As noted above, in some embodiments, the communication device 90 may be provided in the adapter 52 that is configured to couple to the monitor 50 to facilitate wireless communication 103 between the laryngoscope 12 and the monitor 50. The communication between the monitor 50 and the laryngoscope 12, once paired, may be one-way communication, with the laryngoscope 12 receiving physiological parameter information from the monitor 50 but not providing laryngoscope data, e.g., image data, to the monitor 50. In another embodiment, the laryngoscope 12 may communicate the image data to a separate display or device, which may or may not be the monitor 50.

In certain embodiments, the laryngoscope 12 and the monitor 50 include electrical circuitry that operates to process signals, such as signals generated by the camera 70, a coupled introducer 89, and/or control signals provided via inputs, such as the inputs 58, 60 of the monitor 50, or the input 64 on the laryngoscope, for example. In the illustrated embodiment, the processors 80, 94 may be used to execute software. For example, the processor 80 of the laryngoscope 12 receives signals from the camera 70 and executes software to generate an image and/or to carry out any of a variety of processes in accordance with the present disclosure (e.g., display the image, display an introducer image, display or drive activation of a physiological parameter indicator, calculate intubation parameters or alarms, or the like).

The monitor 50 may be a monitor (e.g., a multiparameter monitor, a specialty monitor) that includes on-board processing capability to receive sensor data from one or more communicatively coupled physiological sensors 56 and, using the sensor data, to calculate one or more physiological parameters based on the sensor data. The physiological parameter information communicated from the monitor 50 to the laryngoscope 12 may include sensor data and/or calculated physiological parameters based on the sensor data. The calculated physiological parameter may be in the form of a physiological parameter value (e.g., an oxygen saturation value, a heart rate value, a blood pressure value) or an index or other metric based on the physiological parameter value. In an example, a pulse oximetry sensor generates sensor data indicative of a photoplethysmography waveform that is received by the monitor 50. An oxygen saturation value is calculated by the monitor 50 based on the sensor data and is communicated to the laryngoscope 12. In another example, the monitor 50 may receive already-calculated physiological parameter information, e.g., an already-calculated physiological parameter value, from a coupled medical monitoring device and/or the sensor 56. Accordingly, in such embodiments, the monitor 50 may operate as a pass-through device, and may pass along the already-calculated physiological parameter value to the laryngoscope 12. For example, the monitor 50 may communicate the physiological parameter value in an appropriate communication protocol compatible with the laryngoscope 12. In another embodiment, the monitor 50 may provide the sensor data to the laryngoscope 12, and the laryngoscope 12 may operate on the sensor data to generate the physiological parameter. The monitor 50 may stream or continuously update the physiological parameter information to the laryngoscope 12 while the devices are paired. Accordingly, in an embodiment, a physiological parameter displayed on the monitor 50 or otherwise provided to the caregiver corresponds in real-time to the physiological parameter information of the monitor 50 and communicated to the laryngoscope 12.

In certain embodiments, the monitor 50 may have access to or may display a particular physiological parameter from multiple sensor sources. For example, heart rate may be available via EKG data from an EKG electrode as well as from pulse oximetry data from a pulse oximetry sensor. In an embodiment, the monitor 50 may be programmed to only send the physiological parameter information or physiological parameter value from a single source (e.g., from the EKG sensor or from the pulse oximetry sensor). Alternatively, the monitor 50 may be programmed to arbitrate between multiple available values of a same physiological parameter based on quality metrics. Further, the monitor 50 may operate such that a predetermined sensor 56 or sensor type is a first choice for generating the communicated physiological parameter information when available and the physiological parameter information may be based on sensor data from other available sensors 56 as backups if the first choice is unavailable.

The processors 80, 94 may include multiple microprocessors, one or more "general-purpose" microprocessors, one or more special-purpose microprocessors, and/or one or more application specific integrated circuits (ASICS), or some combination thereof. For example, the processors 80, 94 may include one or more reduced instruction set (RISC) processors. It should be appreciated that the various processing steps may be carried out by either processor 80, 94 or may be distributed between the processors 80, 94 in any suitable manner. The hardware memory 82, 96 may include a volatile memory, such as random access memory (RAM), and/or a nonvolatile memory, such as read-only memory (ROM). It should be appreciated that the hardware memory 82, 96 may include flash memory, a hard drive, or any other suitable optical, magnetic, or solid-state storage medium, other hardware memory, or a combination thereof. The memory 82, 96 may store a variety of information and may be used for various purposes. For example, the memory 82 may store processor-executable instructions (e.g., firmware or software) for the processor 80 to execute, such as instructions for processing signals generated by the camera 70 to generate the image, provide the image on the display screen 22, and/or store the image. The hardware memory 82, 96 may store data (e.g., previously obtained images, time data, etc.), instructions (e.g., software or firmware for generating the images, storing the images, transmitting the images, etc.), and any other suitable data. The memory 82, 96 may store processor-executable instructions (e.g., firmware or software) for the processors 80, 94 to execute, such as instructions for displaying the physiological parameter indicators 28 on the display screen 22.

The laryngoscope 12 may include one or more indicator elements 110 that are separate from the display 20 and that operate to provide the physiological parameter information via a physiological parameter indicator. However, in certain embodiments, the indicator element 110 is not present and the physiological parameter indicator is provided only via the display 20. The indicator element 110 may be a speaker, a haptic feedback element (e.g., a buzzer), one or more light sources, or a combination thereof. The indicator element/s 110 may or may not be provided in conjunction with displayed physiological parameter indicators. The memory 82 of the laryngoscope 12 may store processor-executable instructions (e.g., firmware or software) for the processor 80 to execute, such as instructions for driving the one or more indicator elements 110 to provide the physiological parameter indicator. Accordingly, the processor 80 may provide drive signals to controllers of the one or more indicator elements 110 that are based on the physiological parameter information. In an embodiment, the one or more indicator elements 110 are in a default inactive state and are activated responsive to a physiological parameter value deviating from a predetermined threshold or range (e.g., the one or more indicator elements 110 are activated in response to values lower than or higher than a threshold or outside of a desired range). Additionally or alternatively, in an embodiment, the one or more indicator elements 110 are activated to drive a light source, generate audible tones, and/or drive a haptic element in a manner consistent with the physiological parameter information to provide the physiological parameter indicator when a physiological parameter value is within tolerance of a predetermined threshold or range.

In certain embodiments, the laryngoscope 12 may receive already-calculated physiological parameter values via the monitor 50 and use the received information to drive display or indicator element activation to alert the clinician. In this manner, the laryngoscope 12, which is a handheld, portable device, may not be programmed to store or execute more complex physiological parameter calculation algorithms and to provide more complex display options that are present on the monitor 50, which may increase computational burden and decrease the efficiency of the laryngoscope 12. However, the laryngoscope 12 may be programmed to activate certain functionality when paired with the monitor 50 to operate on the physiological parameter information to generate instructions to provide physiological parameter indicator via the laryngoscope in a manner that is more meaningful for the clinician in the context of airway navigation and that is different than the presentation of the physiological parameter information via the monitor 50. For example, the laryngoscope memory 82 may store processor-executable instructions (e.g., firmware or software) for the laryngoscope processor 80 to execute, such as instructions for identifying deviations from desired predetermined thresholds or ranges of the physiological parameter values. In one embodiment, the deviations may be identified by the monitor 50 and communicated as part of the physiological parameter information to the laryngoscope 12. In another embodiment, the laryngoscope 12 operates on the physiological parameter information according to stored instructions to identify deviations, which in turn may influence the instructions for display of the physiological indicators 28 and/or activation of the one or more indicator elements 110 as provided herein.

Figure 3:
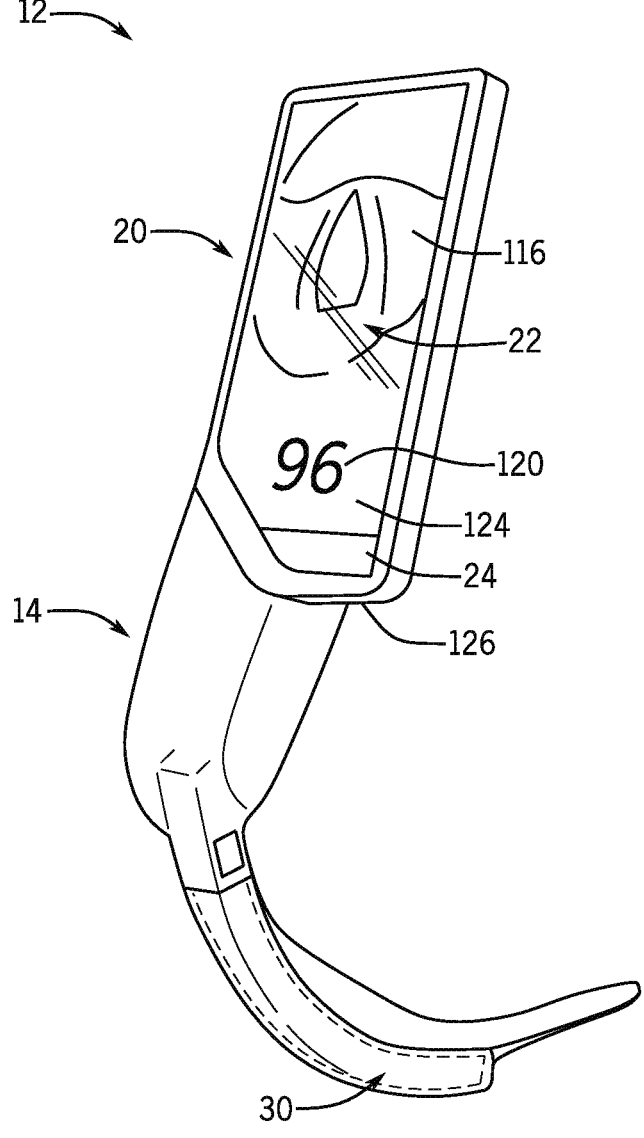
FIG. 3 is a perspective view of a laryngoscope that may be used in conjunction with the system of FIG. 1, in accordance with an embodiment of the present disclosure.

FIGS. 3-8 are examples of different arrangements of the laryngoscope 12 with respect to providing physiological parameter indicators. It should be understood that elements of the various arrangements may be combined or exchanged with one other. FIG. 3 is an example of a laryngoscope 12 in which the display screen 22 shows a captured laryngoscope image 116 via image data generated by a camera 70 of the camera stick 30. A physiological parameter indicator 120 is also displayed as part of the display screen 22 of the display 20, either as an overlay over the laryngoscope image 116 or on a dedicated portion 124 of the display screen 22. The dedicated portion 124 of the display screen 22 may be, in an embodiment, located closer to a distal edge 126 of the lateral portion 24 of the display 20 while a larger portion of the display screen 22 is occupied by the laryngoscope image 116. The physiological parameter indicator 120 may be generally sized and shaped to be clearly discernible by the clinician but without obscuring the laryngoscope image 116. In the depicted embodiment, the physiological parameter indicator 120 is an oxygen saturation value that updates according to the measured values of oxygen saturation from the monitor 50. However, the physiological parameter indicator 120 may be, additionally or alternatively, other types of physiological parameters as provided herein.

Various display features of the physiological parameter indicator 120 may change based on the value of parameter being above or below a predetermined threshold. For example, a color or size of the physiological parameter indicator 120 may be based on the physiological parameter value relative to the predetermined threshold or range. In an embodiment, an animated or graphical effect (e.g., a pulsing effect) may be based on the physiological parameter value or on a value of a different physiological parameter. For example, the displayed oxygen saturation value of the physiological parameter indicator 120 may pulse according to a cadence of a heart rate communicated from the monitor 50 that corresponds to the real-time oxygen saturation. The pulsing may also be related to an oxygen saturation outside of a predetermined threshold or range such that the pulsing only activates to alert the clinician to a dip in oxygen saturation. The pulsing may be a gentle or minor change in color (e.g., pulsing between 100% color to 30-70% color at the heart rate cadence) of the displayed physiological parameter indicator 120 rather than an on/off pulse (e.g., pulsing between 100% color to 0% color) to avoid pulling focus from the laryngoscope image 116. In this manner, multiparameter information (e.g., heart rate and oxygen saturation) is condensed within a limited portion of the display screen 22 to avoid cluttering the display interface and distracting from the laryngoscope image 116. In another example, some or all of the display screen 22, such as the laryngoscope image 116, may pulse to provide physiological parameter information. In such an example, the activation of and/or the rate of pulsing of the laryngoscope image 116 provides physiological parameter information to permit the clinician to remain focused on the laryngoscope image 116 while also receiving additional information based on the characteristics of the pulsing. For example, the laryngoscope image 116 may remain steady (e.g., not pulsing) unless the oxygen saturation value dips below a predetermined threshold, at which point pulsing of the laryngoscope image 116 is activated. In another example, the laryngoscope image 116 pulses according to the heart rate cadence.

Figure 4:
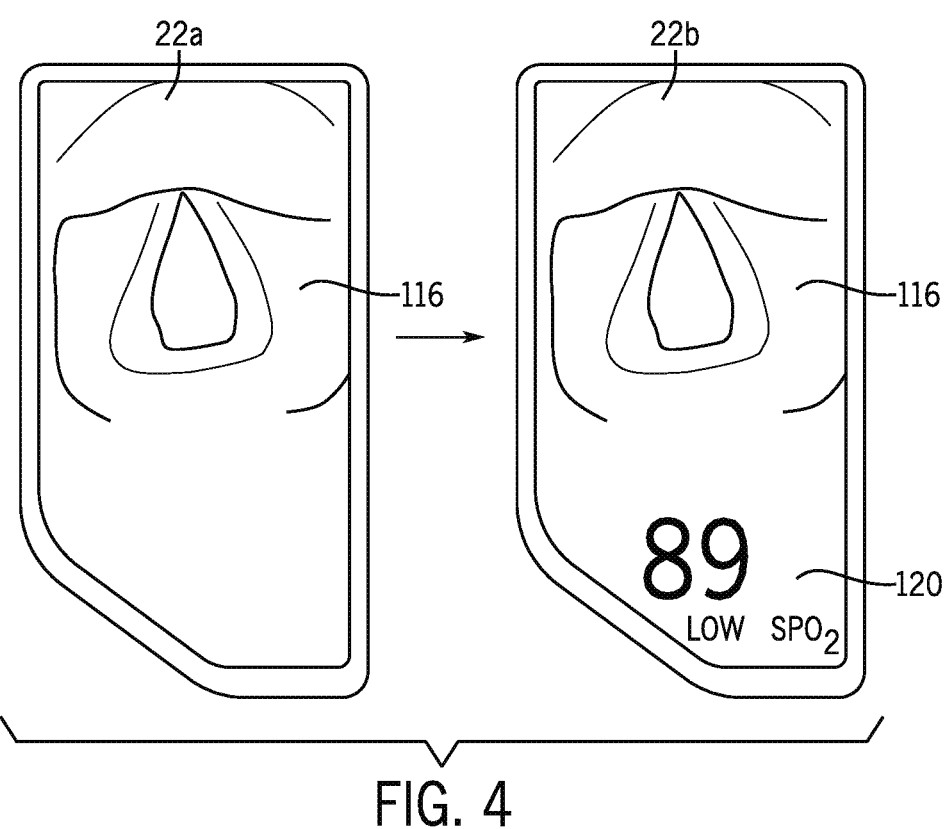
FIG. 4 shows example displays of a laryngoscope that may be used in conjunction with the system of FIG. 1, in accordance with an embodiment of the present disclosure.

FIG. 4 is an embodiment in which the laryngoscope 12 operates to generate the display screen 22a in a default display arrangement when the physiological parameter information is associated with one or more physiological parameter values in a predetermined range or above or below a predetermined threshold. Accordingly, the clinician may focus solely on the laryngoscope image 116 to navigate through the airway in cases in which the physiological parameter or parameters are of no clinical concern with respect to airway navigation or airway procedures. Responsive to an identification of the measured physiological parameter value deviating from a predetermined threshold or range, the display screen 22 automatically (e.g., without user input) transitions to the display screen 22b showing a notification arrangement that includes the displayed physiological parameter indicator 120 displayed together with the laryngoscope image 116. The depicted example shows a low oxygen saturation (SpO$_2$) value that triggers transition to the display screen 22b showing a notification arrangement, by way of example. In the depicted example, the clinician is presented information about the low physiological parameter value without interruption of the airway view from the laryngoscope camera 70.

Once the display screen 22 transitions to the display screen 22b associated with the notification arrangement, the transition may be one-way, such that the physiological parameter indicator 120 is continuously displayed throughout the remainder of the pairing event of the laryngoscope 12 with the monitor 50. That is, even when the value of the physiological parameter returns to a value within a predetermined range or changes to a desired state relative to a predetermined threshold, the notification arrangement of the display 22b such that the clinician may observe whether the updated value is a temporary change or part of a trend to return to desired values. In another embodiment, the display screen 22b associated with the notification arrangement returns to the display screen 22a of the default arrangement when the physiological parameter value is within tolerance of the predetermined range or predetermined threshold according to rules-based logic. In one example, the physiological parameter value being within tolerance for at least a period of time causes return to the display screen 22a of the default arrangement.

Figure 5:
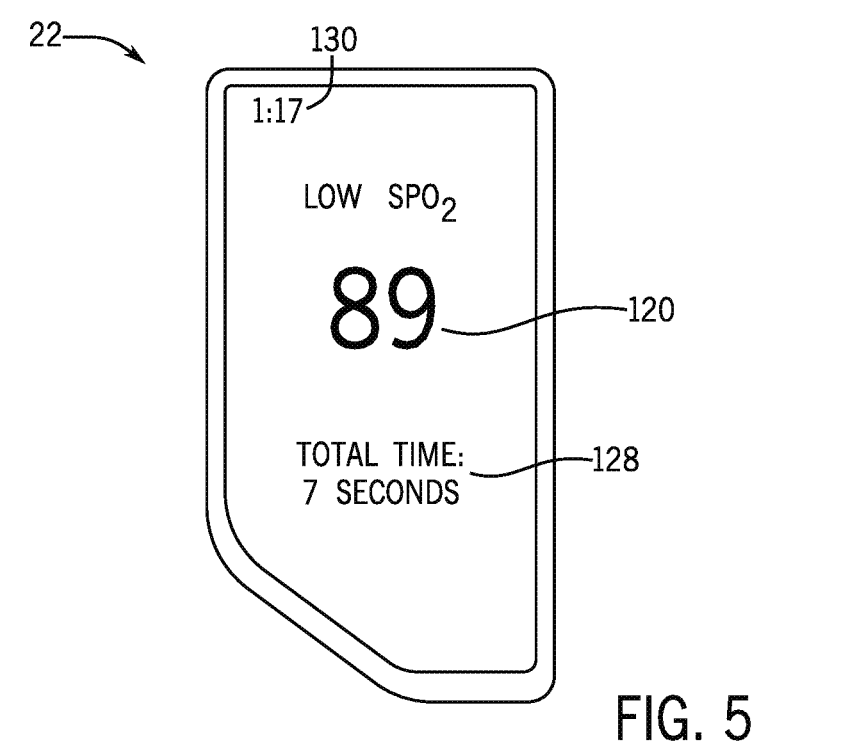
FIG. 5 shows an example of a display of a laryngoscope that may be used in conjunction with the system of FIG. 1, in accordance with an embodiment of the present disclosure.

FIG. 5 shows an alternate arrangement of the display screen 22 in the case of a low oxygen saturation (SpO$_2$) value. The display screen 22 may include one or more time indicators, such as a deviation time indicator 128 reflecting a time spent below a physiological parameter threshold as well as a procedure time indicator 130 reflective of an elapsed time of the intubation procedure. The clinician may provide a user input (e.g., via a user input device 72, such as a touchscreen input on the display screen or a button on the laryngoscope 12) upon a start of the intubation procedure, and the time 91 may keep a procedure clock. The laryngoscope 12 may be programmed to also track total time of deviation, either consecutive or cumulative, of the physiological parameter threshold, which is presented via the deviation time indicator 128. Alternatively, the monitor 50, which may already be tracking this information as part of an alarm determination, may provide the total time of deviation and/or other types of alarm information to the laryngoscope 12 as part of the physiological parameter information, either automatically or responsive to user selections on the monitor 50. By presenting this information via the display screen 22, the clinician need not rely on a sense of how much time has passed during the intubation or rely on clocks that are not synchronized to the start of the intubation procedure.

Figure 6:
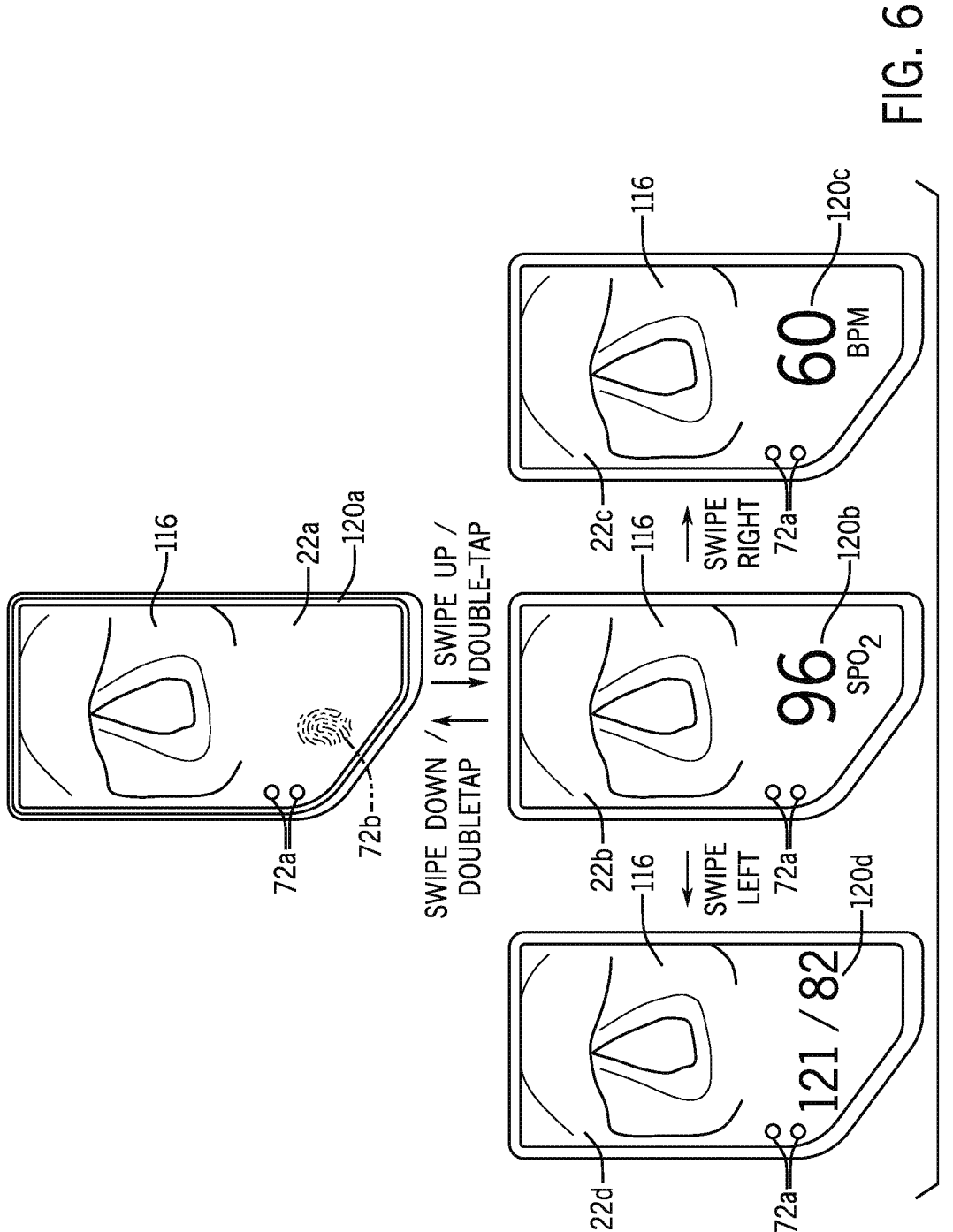
FIG. 6 shows example displays of a laryngoscope that may be used in conjunction with the system of FIG. 1, in accordance with an embodiment of the present disclosure.

In an embodiment, laryngoscope 12 may be programmed to display the physiological parameter indicator and/or cause switching between display of different physiological parameters responsive to user inputs sensed via the user input device/s 72 of the laryngoscope 12. FIG. 6 shows displays screens 22a, 22b, 22c, 22d that are the result of interactions with the user input devices 72. The depicted embodiment may be implemented with touch screen user input devices, such as capacitive sensors of the display screen 22. However, it should be understood that other types of user input devices 72 (e.g., actuatable buttons, voice commands, gyroscopic commands) are also contemplated. The laryngoscope 12 may include certain user input devices, shown as the illustrated devices 72a by way of example, that operate on the laryngoscope image 116 to record the image 116, for example, or that permit entering of user preferences or viewing of a menu. The user input devices 72 may also operate to pair the laryngoscope 12 to the monitor 50. In addition, the display screen 22 may include user input devices 72*b* that transition between different display arrangements of the physiological parameter indicator 120. The default display screen 22*a* may include a less information-rich physiological parameter indicator 120*a* that is associated with a normal or within tolerance physiological parameter value. For example, the physiological parameter indicator 120*a* may be a displayed colored border (as illustrated) around all or part of the laryngoscope image 116 or the perimeter of the display screen 22. The physiological parameter indicator 120*a* may include a graphical effect, such as a partially transparent shading or color tint over all or part of the display screen 22 that may cover all or part of the laryngoscope image 116 or may be located on another portion of the display screen 22. The physiological parameter indicator 120*a* may be a graphical icon that, in embodiments, incorporates the disclosed effects. The color of the border, effect, or other graphical icon may transition between colors or gradients to provide more information. For example, a bright green color may be indicative of higher oxygen saturation values, while a lighter green may indicate downward movement within tolerance, and a transition from green to red indicates a measured deviation. The border, effect, or graphical icon may pulse in cadence with the heart rate while displaying a color associated with the oxygen saturation. In another example, the physiological parameter indicator 120*a* may be a partially transparent shading over all or part of the display screen 22, including portions of the display screen 22 that include the laryngoscope image laryngoscope image 116 and that is sufficiently transparent such that the laryngoscope image 116 is resolvable through the shading.

In certain cases, the clinician may prefer to know the actual value of the physiological parameter, and may swipe up or double-tap the user input 72*b* to transition to the more information-rich display screen 22*b*, which shows the oxygen saturation value as the physiological parameter indicator 120*b*. For example, the clinician may wish to quickly confirm the oxygen saturation value at the initiation of the intubation procedure to confirm that the patient has been adequately preoxygenated before the procedure begins. Once confirmed, the clinician may transition back to the default screen 22*a* by swiping down or double-tapping again. Additionally or alternatively, the clinician may scroll to the left or right to select different physiological parameter indicators. For example, the clinician may swipe right to see the display screen 22*c* associated with the physiological parameter indicator 120*c* of a different physiological parameter (e.g., heart rate) or swipe left to see the display screen 22*d* associated with the physiological parameter indicator 120*d* of another available physiological parameter (e.g., blood pressure).

Figure 7:
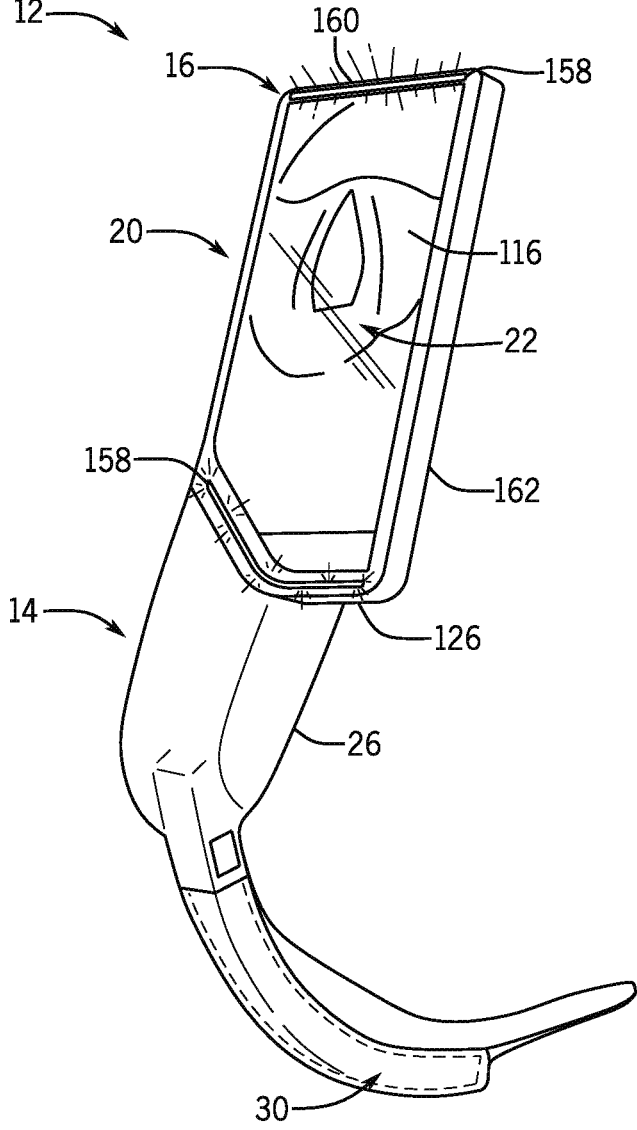
FIG. 7 is a perspective view of a laryngoscope that may be used in conjunction with the system of FIG. 1 and including a light-based physiological parameter indicator on a body of the laryngoscope, in accordance with an embodiment of the present disclosure.

FIG. 7 is an arrangement of the laryngoscope 12 including one or more light-based physiological indicators 158. The light-based physiological indicators 158 include one or more light sources (e.g., LEDs) that are incorporated on or in the housing 26 of the laryngoscope 12. In the depicted embodiment, the light-based physiological indicators 158 are incorporated into a frame 162 of the display 20 at a proximal end 160 and a distal end 126. In this manner, the light-based physiological indicator 158 is in the line of sight of the clinician observing the display 20, but does not necessarily occupy portions of the display screen 22. However, as discussed herein, the light-based physiological indicators 158 may be used in conjunction with other types of physiological parameter indicators, such that the displayed physiological parameter indicator 120 of FIG. 3.

The light sources of the light-based physiological indicator 158 may be responsive to drive signals that are generated based on the physiological parameter information communicated from the monitor 50. In one embodiment, activated lights of a first color (e.g., a green light) are associated with a physiological parameter above a threshold and/or activated lights of a second color (e.g., a red light) are associated with a physiological parameter below a threshold. In an embodiment, the light-based physiological indicator 158 may be in a default inactive state when the physiological parameter is within a predetermined range or does not deviate from a predetermined threshold and is only active to indicate an undesired value. In another embodiment, a pulsing pattern or cadence of the light-based physiological indicator 158 may indicate a heart rate. While the depicted embodiment shows the light-based physiological indicator 158 being on portions of the frame 162 of the display 20, other implementations are also contemplated. For example, the perimeter of the frame 30 may include the light-based physiological indicator 158. In another example, the handle of the body 14 may include the light-based physiological indicator 158. In an embodiment, regardless of the location of the light-based physiological indicator 158, the light sources may be oriented proximally (e.g., towards the proximal end 160) such that the light-based physiological indicator 158 is more visible to the clinician and such that the emitted light does not interfere with an integral light source of the camera stick 30 that is oriented distally.

Figure 8:
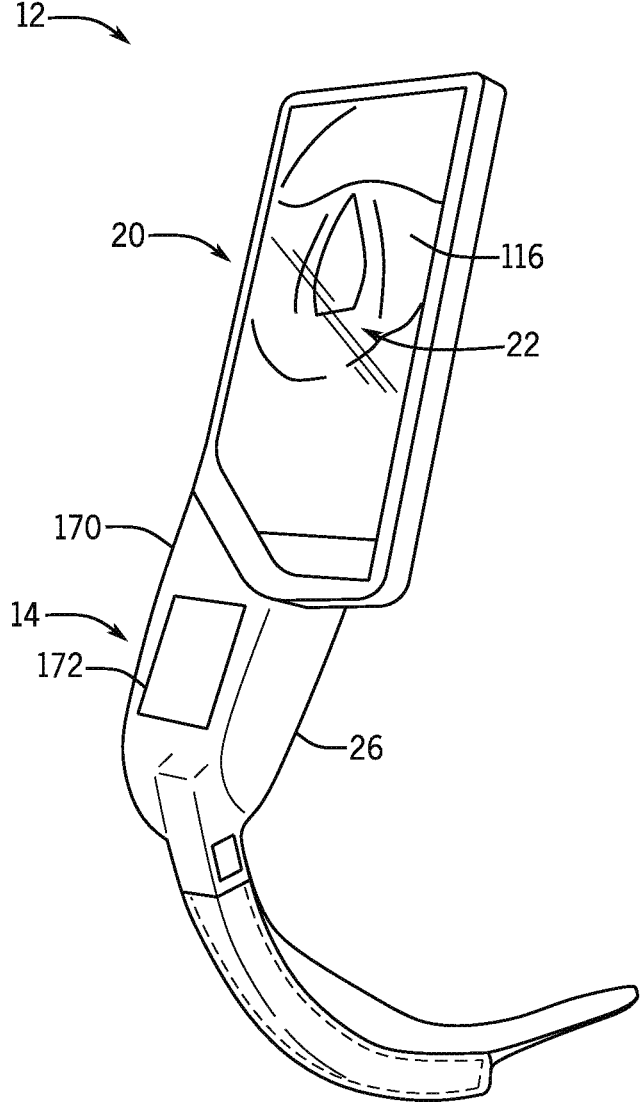
FIG. 8 is a perspective view of a laryngoscope that may be used in conjunction with the system of FIG. 1 and including a haptic physiological parameter indicator on a body of the laryngoscope, in accordance with an embodiment of the present disclosure.

FIG. 8 is an arrangement of the laryngoscope 12 including a haptic feedback element 170 that is integrated into or on the body 14, e.g., on or in the housing 26. As discussed herein, the haptic feedback element 170 may be used in conjunction with other types of physiological parameter indicators, such that the displayed physiological parameter indicator 120 of FIG. 3. The haptic feedback element 170 may be a buzzer or mechanical actuator that is responsive to drive signals that are generated based on the physiological parameter information communicated from the monitor 50. For example, the haptic feedback element 170 may be activated according to a drive signal in which the cycles of active buzzing are coordinated to a heart rate, which each activation corresponding to a heartbeat. In an embodiment, the haptic feedback element 170 may be in a default inactive state when the physiological parameter is within a predetermined range or does not deviate from a predetermined threshold and is only activated to indicate an undesired value, e.g., to alert the clinician that the physiological parameter is outside of the predetermined range. The haptic feedback element 170 may be located on the body 14 in a position that generally corresponds to a handle 172 that is in direct contact with the clinician's hand during operation.

Additionally or alternatively, the indicator element 110 may be a speaker that generates a tone or audible message that serves as the physiological parameter indicator. For example, an activation of the tone or audible message may be indicative of a deviation of a physiological parameter value from the predetermined range or threshold. In another example, a pitch of the tone may be associated with the physiological parameter value, with a high pitch being associated with a deviation and a low pitch being within tolerance. In another example, the tone may pulse at a cadence of a heart rate. While other audible alarms may be present in the patient environment, the speaker may be oriented to be readily discernible by the clinician operating the laryngoscope.

Figure 9:
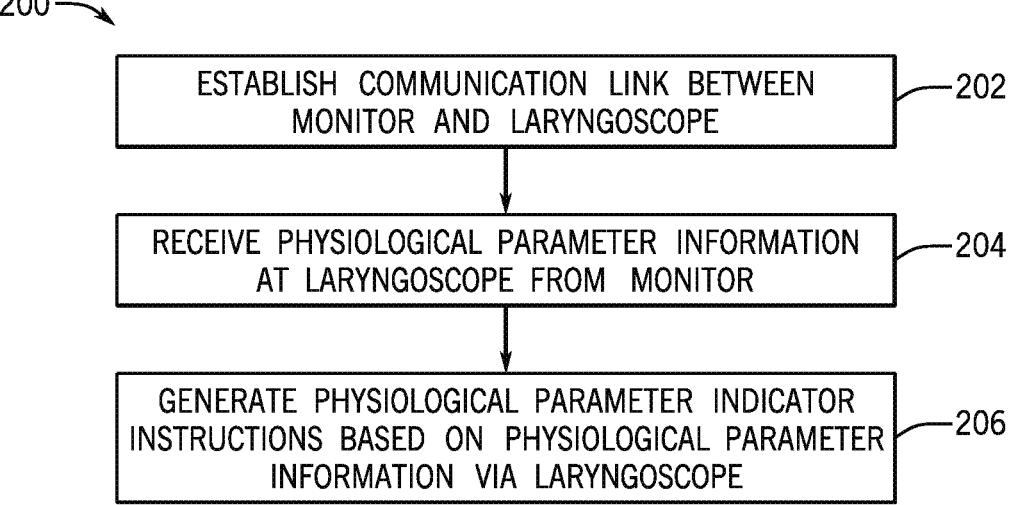
FIG. 9 is a process flow diagram of a method of using the laryngoscope system of FIG. 1, in accordance with an embodiment of the present disclosure.

FIG. 9 is a process flow diagram of a method 200 of using the laryngoscope system 10 of FIG. 1, in accordance with an embodiment of the present disclosure. The method 200 disclosed herein includes various steps represented by blocks. It should be noted that at least some steps of the method 200 may be performed as an automated procedure by a system, such as laryngoscope system 10. Although the flow chart illustrates the steps in a certain sequence, it should be understood that the steps may be performed in any suitable order and certain steps may be carried out simultaneously, where appropriate. Additionally, steps may be added to or omitted from of the method 200. Further, certain steps or portions of the method 200 may be performed by separate devices. For example, a portion of the method 200 may be performed by the processor 80 of the laryngoscope 12, while another portion of the method 200 may be performed by the processor 96 of the monitor 50. In addition, insofar as steps of the method 200 disclosed herein are applied to received signals, it should be understood that the received signals may be raw signals or processed signals. That is, the method 200 may be applied to an output of the received signals, e.g., signals from one or more sensors 56.

With the foregoing in mind, the method 200 of FIG. 9 may begin with establishing communication (e.g., wireless communication) between the laryngoscope 12 and the monitor 50, in step 202. As discussed above, the medical professional may turn the laryngoscope 12 on via a power button, which may be a user input 72 of the laryngoscope 12 and may turn the monitor 50 a power button, which may be a user input 58, 60 of the monitor 50. In some embodiments, once powered on, the laryngoscope 12 and the monitor 50 may automatically establish wireless communication with one another. In some embodiments, the laryngoscope 12 and/or the monitor 50 may provide an indication (e.g., via respective display screens 22, 54) upon establishing wireless communication with one another. In some embodiments, the medical professional may provide inputs (e.g., via user inputs) to adjust or to select the appropriate device(s) (e.g., the monitor 50 or the laryngoscope 12) that should communicate with one another during the laryngoscopy procedure.

In step 204, the monitor 50 provides physiological parameter information to the laryngoscope 12. For example, the processor 94 of the monitor 50 may access the physiological parameter information from a memory 96 and may provide the physiological parameter information to the communication circuitry 102 to be transmitted to the laryngoscope 12. The communication circuitry 90 of the laryngoscope receives the physiological parameter information and provides the physiological parameter information to the processor 80 to be used to generate instructions related to a physiological parameter indicator at step 206. For example, the processor 80 may operate on the physiological parameter information to generate a display screen 22 and/or to drive an indicator element 110. As updated physiological parameter information is available, the method 200 repeats step 204 and step 206 to generated updated physiological parameter indicator instructions.

In some embodiments, the physiological parameter information includes or is operated on to generate a physiological parameter value, and the physiological parameter value is identified by the monitor 50 or the laryngoscope 12 as being within tolerance of a predetermined range or relative to a predetermined threshold or as deviating from the predetermined range or relative to a predetermined threshold. For example, in an embodiment, an oxygen saturation value above 90 is considered to within a predetermined desired range while oxygen saturation of 90 or below is considered to deviate from the predetermined range or relative to a predetermined threshold. The predetermined range or predetermined threshold may be part of stored instructions in the monitor 50 that are provided as part of the physiological parameter information. In another embodiment, the predetermined range or predetermined threshold may be part of stored instructions in the laryngoscope 12, and the laryngoscope 12 operates to identify conformance or deviation from the predetermined range or predetermined threshold for the physiological parameter value of interest. Once identified, the conformance or deviation may be part of the instructions to provide the physiological parameter indicator as provided herein.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

What is claimed is:

1. A laryngoscope, comprising:
a camera;
a body having a housing;
a display, attached to the body, configured to display image data from the camera;
communication circuitry configured to receive physiological parameter information from a paired monitor; and
a processor programmed to generate instructions to:
display image data on the display without displaying a physiological parameter indicator; and
display the physiological parameter indicator via the laryngoscope, in response to determining that the physiological parameter information received from the paired monitor comprises a physiological parameter value that deviates from a threshold, wherein the physiological parameter indicator is displayed without obscuring the image data by displaying the physiological parameter indicator in a dedicated portion of the display; and
cause removal of the display of the physiological parameter indicator based on a user input on the display.

2. The laryngoscope of claim 1, further comprising a haptic feedback element, and wherein the processor is further programmed to generate drive instructions of the haptic feedback element based on the determination that the physiological parameter value deviates from the threshold.

3. The laryngoscope of claim 2, further comprising a handle coupled to the display, and wherein the haptic feedback element is disposed on or in the handle.

4. The laryngoscope of claim 2, wherein the physiological parameter information comprises a current heart rate value for a patient, and wherein the drive instructions of the haptic feedback element activate the haptic feedback element at a cadence of the heart rate value to indicate the current heart rate value.

5. The laryngoscope of claim 1, wherein the processor is programmed to generate instructions to display the physiological parameter indicator while displaying the image data from the camera.

6. The laryngoscope of claim 5, wherein the physiological parameter indicator is a physiological parameter value.

7. The laryngoscope of claim 1, further comprising a light source separate from the display, and wherein the processor is further programmed to generate drive instructions of the light source based on the determination that the physiological parameter value deviates from the threshold.

8. The laryngoscope of claim 1, wherein the processor is further programmed to remove the physiological parameter indicator from the display in response to determining that the physiological parameter information no longer deviates from the threshold.

9. The laryngoscope of claim 1, wherein the physiological parameter information comprises an oxygen saturation value, and wherein the display is configured to pulse responsive to the oxygen saturation value being below the threshold.

10. The laryngoscope of claim 1, further comprising a speaker, and wherein the processor is further programmed to generate instructions to drive the speaker based on the physiological parameter information.

11. A system comprising:
   a monitor comprising monitor communication circuitry and configured to communicate physiological parameter information; and
   a laryngoscope comprising:
      a camera;
      a touchscreen display configured to display image data from the camera and to receive a touch input;
      communication circuitry configured to pair to the monitor to receive physiological parameter information from the monitor; and
      a processor programmed to generate instructions to:
         detect a first touch input received by the touchscreen display of the laryngoscope;
         display a physiological parameter indicator via the display of the laryngoscope based on the first touch input and based on the received physiological parameter information from the monitor, wherein the physiological parameter indicator is displayed in a lower corner of the touchscreen display to avoid obscuring the image data;
         detect a second touch input received by the touchscreen display of the laryngoscope; and
         in response to the second touch input, remove the physiological parameter indicator from display.

12. The system of claim 11, wherein the physiological parameter information comprises a physiological parameter value that is calculated by the monitor, and wherein the physiological parameter indicator is displayed in a lower right-hand corner of the display.

13. The system of claim 12, wherein the monitor comprises a monitor display that displays the physiological parameter value based on the physiological parameter information, and wherein the physiological parameter value is simultaneously displayed on the display of the laryngoscope as the physiological parameter indicator.

14. The system of claim 12, wherein the processor is programmed to generate instructions to display the physiological parameter value on the display of the laryngoscope only upon a determination that the physiological parameter value that deviates from a predetermined threshold or range.

15. The system of claim 11, further comprising a sensor coupled to the monitor and configured to generate sensor data upon which the physiological parameter information is based, wherein the sensor is a pulse oximetry sensor, and wherein the sensor data comprises a photoplethysmography waveform.

16. The system of claim 11, wherein the laryngoscope is configured to receive a user input upon an initiation of a medical procedure and a timer, wherein the processor is configured to receive a medical procedure elapsed time based on the user input and the timer and generate instructions to modify the physiological parameter indicator based on the medical procedure elapsed time and the physiological parameter information.

17. A laryngoscope, comprising:
   a camera;
   a touch-sensitive display of the laryngoscope configured to display image data from the camera;
   communication circuitry configured to receive physiological parameter information from a paired monitor; and
   a processor programmed to:
      receive a first touch input, comprising at least one of a tap or a swipe, on the touch-sensitive display of the laryngoscope;
      in response to the first touch input, display on the touch-sensitive display of the laryngoscope a physiological parameter indicator based on the physiological parameter information received from the paired monitor, the physiological parameter indicator being displayed on the laryngoscope simultaneously with the image data from the camera, wherein the physiological parameter indicator is displayed as an overlay without obscuring the image data;
      receive a second touch input, comprising at least one of a tap or a swipe, on the touch-sensitive display; and
      in response to the second touch input, remove the physiological parameter indicator from the display.

18. The laryngoscope of claim 17, wherein the first touch input is a double-tap input.

19. The laryngoscope of claim 17, wherein the physiological parameter indicator is graphical icon.

20. The laryngoscope of claim 17, wherein the physiological parameter indicator indicates an oxygen saturation value.

21. The laryngoscope of claim 1, wherein the dedicated portion is in a lower right-hand corner of the lateral portion.

22. The system of claim 11, wherein first touch input is a first tap and the second touch input is a second tap.

* * * * *